United States Patent [19]

Fox et al.

[11] Patent Number: 4,841,015

[45] Date of Patent: Jun. 20, 1989

[54] LOW PLATE-OUT POLYCARBONATE END CAPPED WITH PHENOXY ACETIC ACID

[75] Inventors: Daniel W. Fox, Pittsfield; Edward N. Peters, Lenox; Paul D. Sybert, Pittsfield, all of Mass.

[73] Assignee: General Electric Company, Mt. Vernon, Ind.

[21] Appl. No.: 136,664

[22] Filed: Dec. 22, 1987

[51] Int. Cl.$^4$ ............................................. C08G 63/62
[52] U.S. Cl. .................................... 528/198; 528/196
[58] Field of Search .......................................... 528/198

[56] References Cited

U.S. PATENT DOCUMENTS

| 4,431,793 | 2/1984 | Rosenquist ........................... | 528/198 |
| 4,446,296 | 5/1984 | Rosenquist ........................... | 528/198 |
| 4,448,953 | 5/1984 | Rosenquist et al. ................. | 528/198 |

FOREIGN PATENT DOCUMENTS 1123625  6/1986  Japan .

Primary Examiner—Harold D. Anderson
Attorney, Agent, or Firm—Martin Barancik; Joseph T. Eisele

[57] ABSTRACT

Polycarbonate resins are chain-terminated with a group selected from those of the formula:

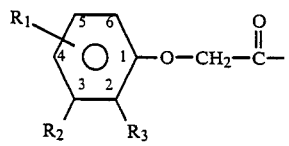

wherein $R_1$, $R_2$ and $R_3$ are each independently selected from the group consisting of hydrogen, halogen, hydrocarbyl of from 1 to 12 carbon atoms, inclusive; and halogen-substituted hydrocarbyl of 1 to 12 carbon atoms, inclusive; $R_1$ is attached to a ring carbon atom at one of the 4, 5 or 6 positions; and $R_2$ and $R_3$ when taken together represent the divalent moiety of formula:

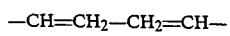

which effectively creates an additional fused aromatic ring structure. The resins exhibit a low plate-out when processed thermally.

8 Claims, No Drawings

LOW PLATE-OUT POLYCARBONATE END CAPPED WITH PHENOXY ACETIC ACID

BACKGROUND OF THE INVENTION

1. Field of The Invention

The invention relates to aromatic carbonate polymers of controlled molecular weight and more particularly relates to such polymers end-capped with a class of aromatic carboxylic acids or equivalent acid chlorides.

2. Brief Description of the Prior Art

It is known that in certain procedures of producing aromatic carbonate polymers from dihydric phenols and a carbonate precursor such as phosgene small amounts of certain weight regulators or chain terminators can be used to provide end or terminal groups on the carbonate polymer and thereby control the molecular weight of the polycarbonate. Such materials include phenol and p-tertiary-butylphenol.

The prior art also disclosed several other types of compounds that act as chain terminators for the carbonate polymers. Thus, U.S. Pat. No. 3,085,992 discloses alkanol amines as chain terminators; U.S. Pat. No. 3,399,172 teaches imides as chain terminators; U.S. Pat. No. 3,275,601 discloses that aniline and methyl aniline function as chain terminators in the interfacial polymerization process for producing polycarbonates; and U.S. Pat. No. 4,001,184 discloses primary and secondary amines as molecular weight regulators for polycarbonate. Furthermore, U.S. Pat. No. 3,028,365 discloses that aromatic amines and other monofunctional compounds can be used to control or regulate the molecular weight of the polycarbonates, thereby forming aryl carbonate terminal groups. Aromatic polycarbonates having carbonate end groups are disclosed in U.S. Pat. No. 4,111,910. These polycarbonates are prepared using a terminating amount of ammonia, ammonium compounds, primary cycloalkyl, aliphatic or aralkyl amines and secondary cycloaklkyl, alkyl or aralkyl amines.

However, according to Schnell, Chemistry and Physics of Polycarbonates (1964), page 183, ammonium hydroxide and amines saponify polycarbonates back to the monomers, i.e., bisphenol A. This is supported by Bolgiano in U.S. Pat. No. 3,223,678 wherein he indicates that small amounts of amines such as monoethanolamine and morpholine break or degrade polycarbonates into lower molecular weight polycarbonates. Thus, this area of chemistry is generally not very well understood and is one where the empirical approach is still generally the method used to determine whether a particular compound or class of compounds will function as effective chain terminators or terminal groups in polycarbonate. This area is yet further complicated by the fact that, even though a particular compound may be a chain terminator, its presence as a terminal group in the polycarbonate polymer may adversely affect the physical properties of the polycarbonate or molding compositions of polycarbonates.

A more recent improvement in the prior art is represented by the use of aroyl halides to terminate polycarbonate resin chains; see U.S. Pat. No. 4,448,953 to Rosenquist, et al. However, many other improvements are sought over prior art methods for polycarbonate chain termination. For example, the use of phenols as chain terminators in the preparation of polycarbonates leads to the formation of significant levels of the corresponding diaryl carbonates as contaminants. Because of the volatility of these diaryl carbonates, they "plate out" during thermal processing onto the molds and processing equipment, i.e.; they condense on the surfaces of the molds, the processing equipment and also onto the surface of the molded article itself.

We have now found that the use of certain carboxylic acids and acid chlorides as terminators in the preparation of polycarbonates affords resins with lower plate-out. The use of these low plate-out resins will reduce molding down time, thus affording higher productivity of a given resin processing line.

In addition, mixtures of various carboxylic acids can be used to fine tune the properties of the resin. For example, stearic acid may be used with benzoyl chloride to afford a low plate-out resin with improved release properties. Other advantages of the invention will be described below.

SUMMARY OF THE INVENTION

The invention comprises an aromatic polycarbonate resin having a polymer chain terminated with a monovalent group of the formula:

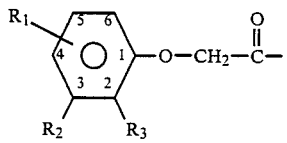

wherein $R_1$, $R_2$, and $R_3$ are each independently selected from the group consisting of hydrogen, halogen, hydrocarbyl having from 1 to 12 carbon atoms, inclusive and halogen substituted hydrocarbyl of 1 to 12 carbon atoms, inclusive; R, is attached to a carbon atom at one of the ring positions 4, 5 or 6; and $R_2$, and $R_3$ when taken together represent the divalent moiety of the formula:

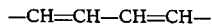

which effectively creates an additional fused aromatic ring structure. Preferably $R_2$, and $R_3$ are each hydrogen and $R_1$ is selected from the group consisting of halogen, alkyl of 1 to 8 carbon atoms, inclusive and alkaryl; most preferably chlorine, methyl, t-butyl, octyl or p-cumyl.

The polymers of the invention are useful as thermoplastically moldable resins, having a reduced quantity of many plate-out disadvantages.

The term "halogen" is used herein in its normal sense as embracive of chlorine, bromine and iodine.

The term "hydrocarbyl" as used herein means the monovalent moiety obtained upon removal of a hydrogen atom from a parent hydrocarbon. Representative of hydrocarbyl are alkyl of 1 to 12 carbon atoms, inclusive, such as methyl, ethyl, propyl, butyl, pentyl, hexyl, heptyl, octyl, nonyl, undecyl, decyl, dodecyl and the isomeric forms thereof; cycloalkyl of 3 to 8 carbon atoms, inclusive such as cyclopropyl, cyclobutyl, cyclopentyl, cyclohexyl, cycloheptyl, cyclooctyl and the like; alkyl substituted cycloalkyl of 4 to 12 carbon atoms, inclusive, such as 2-methylcyclopropyl, 3,4-dimethylcyclohexyl; aryl of 6 to 10 carbon atoms such as phenyl, naphthyl; aralkyl of 7 to 10 carbon atoms, inclusive, such as benzyl, phenethyl, phenpropyl, phenbutyl and the like; alkaryl of 7 to 10 carbon atoms, inclusive, such as methylphenyl, ethylphenyl, propylphenyl, butylphenyl and the like.

The term "halogen substituted hydrocarbyl" as used herein means hydrocarbyl as defined above wherein one or more hydrogen atoms have been replaced with a halogen atom.

The compositions of the invention are useful for injection molding of complex parts such as tool The compositions of the invention are useful for injection molding of complex parts such as tool housing, parts for automobile bodies, and the like.

DETAILED DESCRIPTION OF THE PREFERRED EMBODIMENTS OF THE INVENTION

The aromatic carbonate polymers employed in the practice of this invention are thermoplastically moldable carbonate homopolymers of dihydric phenols, carbonate copolymers of two different dihydric phenols or copolymers of such dihydric phenols with glycols, e.g., ethylene glycol or propylene glycol.

These polycarbonates and their preparation are known in the art and are described, for example, in U.S. Pat. Nos. 3,028,365; 3,334,154; 3,275,601 and 3,915,926, all of which are incorporated herein by reference. Generally, such aromatic carbonate polymers are prepared by reacting a dihydric phenol with a carbonate precursor. The dihydric phenols employed are known, and in which the reactive groups are the two phenolic hydroxyl groups. Some of these are represented by the general formula:

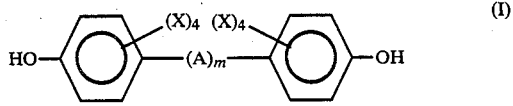

wherein A is a divalent hydrocarbon radical containing from 1 to about 15 carbon atoms; a substituted divalent hydrocarbon radical containing from 1 to about 15 carbon atoms and substituent groups such as halogen;

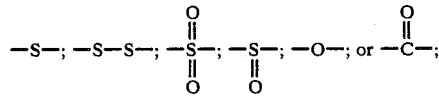

wherein each X is independently selected from the group consisting of hydrogen, halogen, and a monovalent hydrocarbon radical such as an alkyl group of from 1 to about 8 carbon atoms, an aryl group of from 6–18 carbon atoms, an aralkyl group of from 7 to about 14 carbon atoms, an alkaryl group of from 7 to about 14 carbon atoms, an oxyalkyl group of from 1 to about 8 carbon atoms, or an oxyaryl group of from 6 to 18 carbon atoms; and wherein m is zero or 1.

Typical of some of the dihydric phenols that can be employed in the practice of the present invention are bis-phenols such as (4-hydroxyphenyl)methane, 2,2-bis(4-hydroxyphenyl)propane (also known as bisphenol A), 2,2-bis(4-hydroxy-3-methylphenyl) propane, 4,4-bis (4-hydroxyphenyl)heptane, 2,2-bis(4-hydroxy-3,5-dichlorophenyl)propane, 2,2-bis(4-hydroxy-3,5-dibromophenyl) propane; dihydric phenol ethers such as bis(4-hydroxyphenyl)ether, bis(3,5-dichloro-4-hydroxyphenyl) ether; dihydroxydiphenyls such as p,p'- dihydroxydiphenyl, 3,3'-dichloro-4,4'-dihydroxydiphenyl, etc.; dihydroxyaryl sulfones such as bis(4-hydroxyphenyl) sulfone, bis(3,5-dimethyl-4-hydroxyphenyl)sulfone, dihydroxy benzenes, resorcinol, hydroquinone, halo- and alkyl-substituted dihydroxy benzenes such as 1,4-dihydroxy-2,5-dichlorobenzene, 1,4-dihydroxy-3-methylbenzene, etc.; and dihydroxy diphenyl sulfides and sulfoxides such as bis (4-hydroxyphenyl) sulfide and bis (4-hydroxyphenyl) sulfoxide, bis(3,5-dibromo-4-hydroxyphenyl)sulfoxide. A variety of additional dihydric phenols are available and are disclosed in U.S. Pat. Nos. 2,999,835; 3,028,365 and 3,153,008; all of which are incorporated herein by reference. It is, of course, possible to employ two or more different dihydric phenols or a combination of a dihydric phenol with glycol.

The carbonate precursor can be either a carbonyl halide, a diarylcarbonate or a bishaloformate. The carbonyl halides include carbonyl bromide, carbonyl chloride, and mixtures thereof. The bishaloformates suitable for use include the bishaloformates of dihydric phenols such as bischloroformates of 2,2-bis(4-hydroxyphenyl)-propane, 2,2-bis(4-hydroxy-3,5-dichlorophenyl)propane, hydroquinone, and the like, or bishaloformates of glycols such as bishaloformates of ethylene glycol, and the like. While all of the above carbonate precursors are useful, carbonyl chloride, also known as phosgene, is preferred.

Also included within the scope of the present invention are the high molecular weight thermoplastic randomly branched polycarbonates. These randomly branched polycarbonates are prepared by coreacting a polyfunctional organic compound with the aforedescribed dihydric phenol and carbonate precursor. The polyfunctional organic compounds useful in make the branched polycarbonates are set forth in U.S. Pat. Nos. 3,635,895 and 4,001,184, which are incorporated herein by reference. These polyfunctional compounds are generally aromatic and contain at least three functional groups which are carboxyl, carboxylic anhydride, haloformyl or mixtures thereof. Some nonlimiting examples of these polyfunctional aromatic compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride or trimellitic acid or their haloformyl derivatives. Also included herein are blends of a linear polycarbonate and a branched polycarbonate.

The instant invention is directed to novel carbonate polymers having as terminal or end groups particular monovalent moieties of the formula:

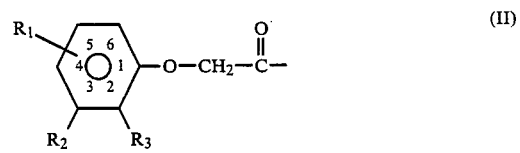

wherein $R_1$, $R_2$ and $R_3$ have the meanings previously ascribed to them. The moieties of the formula (II) given above are the residue after reaction of the terminal end of the polycarbonate polymer chain with a carboxylic acid of the formula:

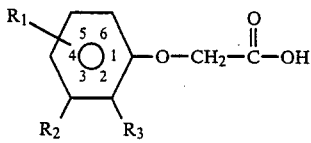

(III)

wherein $R_1$, $R_2$ and $R_3$ have the meanings ascribed to them above; or the corresponding acyl halide. Compounds of the formula (III) and the corresponding acyl halides are well known compounds as are methods of their preparation. Representative of the compounds of formula (III) are phenoxyacetic acid, 4-chlorophenoxyacetic acid, 2,4-dichlorophenoxyacetic acid, 2,4,6-trichlorophenoxyacetic acid, 4-methylphenoxyacetic acid, 3,5-dimethylphenoxyacetic acid, 4-p-tert-butylphenoxyacetic acid, 3-octylphenoxyacetic acid, 4-phenylphenoxyacetic acid, 4-(p-chlorophenyl)-phenoxyacetic acid, 4-p-cumylphenoxyacetic acid, naphthoxyacetic acid and the like. The corresponding acyl halides may be prepared by acylation of the acid of formula (III) using known methods; see for example the method of Cloke et al., JACS 53, 2794 (1931).

The novel carbonate polymers of the instant invention are prepared by reacting at least one compound of Formula (III) or the corresponding acyl halide with a dihydric phenol and a carbonate precursor. During the polymerization reaction the compounds of Formula (III) react with the dihydric phenol to form the end groups present in the polymer.

Only one compound of Formula III may be used, in which case all of the end groups on the polymers will be the same, or two or more different compounds of Formula III may be used in conjunction with known phenol and tertiary butylphenol chain terminators. In such instance the polymers will contain a mixture of end groups formed by the reaction of the various end capping agents with the polymer. The amount of the particular end capping agent used is determinative of the ratio of the resultant end groups present in the polymer.

The method for preparing the aromatic carbonate polymer of this invention, when employing phosgene, involves passing phosgene into a reaction mixture containing a dihydric phenol, an acid acceptor, and at least one compound of Formula III. The compound of Formula III can be present before the introduction of the phosgene or it may be added after introduction of the phosgene has commenced.

A suitable acid acceptor may be either organic or inorganic in nature. Representative of an organic acid acceptor is a tertiary amine such as pyridine, triethylamine, dimethylaniline, tributylamine and the like. The inorganic acid acceptor may be one which can be either a hydroxide, a carbonate, a bicarbonate, or a phosphate or an alkali or alkaline earth metal hydroxide. Also present in the reaction mixture may be a catalyst. The catalysts which are employed herein can be any of the catalysts that aid the polymerization of bisphenol A with phosgene. Representative catalysts include tertiary amines, secondary amines, quaternary ammonium compounds, quaternary phosphonium compounds, amidines and the like.

The temperature at which the phosgenation reaction proceeds may vary from below 0° C. to above 100° C. The reaction proceeds satisfactorily at temperatures from room temperature (25° C.) to 50° C. Since the reaction is exothermic, the rate of phosgene addition may be used to control the reaction temperature. The amount of the phosgene required will generally depend upon the amount of the dihydric phenol present. Generally speaking, one mole of phosgene will react with one mole of the dihydric phenol to provide the polymer and two moles of HCl. Two moles of HCl are in turn "attached" by the acid acceptor present. The foregoing are herein referred to as stoichiometric or theoretical amounts.

A feature of the invention is that the compounds of Formula III react with the carbonate polymer to provide a polycarbonate having improved processing properties (low-or no-plate-out). The weight average molecular weight, for example, can be controlled between about 1,000 and about 200,000 depending upon the amount of the compound of Formula III employed. Generally, the greater the amount of the compound of Formula III employed in the reaction mixture the lower the molecular weight of the carbonate polymer. Conversely, the smaller the amount of the compound of Formula III employed the larger the molecular weight of the polycarbonate. The amount of the compound of the formula (III) employed is a terminating amount. By terminating amount is meant an amount effective to terminate the chain length of the carbonate polymer before the molecular weight of the polymer becomes too high and, consequently, the polymer becomes too viscous for any practical application, but insufficient to terminate the polymer chain before a polycarbonate of useful molecular weight is formed. Generally, this amount ranges from between about 1 to about 10 mole percent based on the amount of the dihydric phenol present, preferably from about 1 to 7 mole %.

The following examples and preparations describe the manner and process of making and using the invention and set forth the best mode contemplated by the inventor of carrying out the invention but are not to be construed as limiting the invention. Where reported, the following tests were carried out.

Intrinsic Viscosity (I.V.)

The intrinsic viscosity was measured at a temperature of 25° C. in chloroform and is reported in deciliters/gram (dl/g).

Plate-Out

Plate-out is determined with the assistance of Fourier Transform Infra-red Spectroscopy (FTIR). The procedures consists of placing 2.6 grams of the polymer being examined in a vial. A silver chloride FTIR slide is placed over the mouth of the vial, which is then placed in the confines of a hot steel block (temperature 340°) having a depth of 2.54 cm., for 8 minutes. Plate-out, if any, condenses on the silver chloride slide, for reading by the aforesaid spectroscopic technique and are given by weight.

Molecular Weight (Mw) and Number (Mn)

The weight average molecular weight (Mw) and number average molecular number (Mn) were determined by gel permeation chromatography (GPC) in chloroform relative to polystyrene standards using a UV detector at 254 nm.

Kasha Index (KI)

The KI of a resin is a measurement of its melt viscosity and is obtained in the following manner: a film of the resin is pressed at 550° C. and provided. Seven grams of film resin, dried a minimum of 90 minutes at 125° C., are added to a modified Tinius-Olsen model T3 melt indexer; the temperature in the indexer is maintained at 250° C. and the resin is heated at this temperature for 6 or 12 minutes, after 6 or 12 minutes the resin is forced through a 0.04125 inch radius orifice using a plunger of radius 0.1865 inch and an applied force of 17.7 lbs.; the time required for the plunger to travel two inches is measured in centiseconds; that is reported as the KI.

Glass Transition Temperature (Tg)

The glass transition temperatures were determined by using a Perkin-Elmer DSC-2B instrument which measures the glass transition temperature or (Tg) by differential scanning calorimetry.

EXAMPLE 1

This example illustrates a polycarbonate end-capped with a prior art compound and thus falling outside the scope of the present invention.

To a reactor fitted with a mechanical agitator are charged 450 ml of deionized water, 600 ml of methylene chloride, 91.3 grams (0.40 moles) of bisphenol A, 1 milliliter of triethylamine, and 4.42 gms (0.02 moles) of p-tert-butyl-phenol (5 mol %). Phosgene is introduced at the rate of 1.25 g/min. and phosgenation is continued for 34 minutes. The pH is maintained at between 10.5 and 11.5 by the addition of 25% aqueous sodium hydroxide. After phosgenation has ceased, the mixture is stirred for 10 minutes at a pH of 11 and then the brine layer is separated by centrifuge and the resin solution is washed with aqueous acid and water. The resin is precipitated in hot water and dried at a temperature of 125° C.

EXAMPLE 2

The procedure of Example 1, supra., is repeated except that the p-tert-butylphenol as used therein is replaced with 5.3 mol % of 2,4-dichlorophenoxyacetic acid. The polymer is characterized by an I.V. of 0.394 dl/g; a K.I. of 4,446; a Tg of 139° C.; a Mw of 36,000 and a Mn of 6000. Representative samples of the polymers obtained in each of Examples 1 and 2 were tested for plate-out. The end-capped polycarbonate of Example 2 did not exhibit any plate-out. The phenol capped polycarbonate of Example 1 afforded 0.01 mg of plate-out/g of polymer; the plate-out was shown by FTIR to be the diaryl carbonate.

EXAMPLE 3

The procedure of Example 1, supra., is repeated except that the p-tert-butylphenol as used therein is replaced with 2.8 mol % of 2,4-di-t-butylphenoxyacetic acid. The polymer is characterized by an IV of 0.63 dl/g; a Tg of 152° C.; a Mw of 66,800 and a Mn of 14,600.

EXAMPLE 4

The procedure of Example 1, supra., is repeated except that the p-tert-butylphenol as used therein is replaced with 2.8 mol % of 3,5-di-t-butylphenoxyacetic acid. The polymer is characterized by an IV of 0.52 dl/g; a Tg of 147° C.; a Mw of 56,300 and a Mn of 13,800.

EXAMPLE 5

The procedure of Example , supra., is repeated except that the p-tert-buytlphenol as used therein is replaced with 2.8 mol % of 2,4-dicumylphenoxyacetic acid. The polymer is characterized by an IV of 0.55 dl/g; a Tg of 146° C.; a Mw of 58,200 and a Mn of 13,600.

EXAMPLE 6

Preparation of 2,4-dicumylphenoxyacetic acid

In a 500 ml three neck flask equipped with mechanical stirrer, nitrogen inlet and Dean-Stark trap/condenser was added 40.0 grams (0.121 moles) 2,4-dicumylphenol, 150 ml dimethylsulfoxide (DMSO), 0.121 moles of sodium hydroxide (9.68 grams of 50% aqueous NaOH), and 100 ml toluene. The mixture is stirred and heated to azeotropically remove water. After water removal is complete the temperature is lowered to about 90° C. and 14.10 grams (0.121 moles) of the sodium salt of chloroacetic acid is added. The reaction is stirred at 90° C. for 16 hours. The product is isolated by cooling and pouring the reaction mixture into 500 ml of a 2% aqueous hydrochloric acid. After filtration, washing with water and drying a white powder was obtained which exhibited a melting point of 114° C.

EXAMPLE 7

Preparation of 2,4-di-tert-butylphenoxyacetic acid

Following the procedure for 2,4-di-cumylphenoxyacetic acid given above, except employing 40.0 grams (0.194 moles) 2,4-di-tert-butyl phenol; 0.194 moles sodium hydroxide; and 22.58 grams (0.194 moles) sodium salt chloroacetic acid, there is obtained after isolation and crystallization from toluene a material exhibiting a melting point of 175° C. and 100% relative purity by gas chromatography.

EXAMPLE 8

Preparation of 3,5-di-tert-butylphenoxyacetic acid

Following the procedure for 2,4-dicumylphenoxyacetic acid given above except using; 30.10 grams (0.146 moles) 3,5-di-tert-butylphenol; 0.146 moles sodium hydroxide; and 17.0 grams (0.146 moles) sodium salt of chloroacetic there is obtained a product which upon isolation gave a white powder exhibiting a melting point of 134° C. and 99.6% relative purity by gas chromatography.

What is claimed is:

1. An aromatic polycarbonate resin having a polymer chain terminated with a monovalent group of the formula:

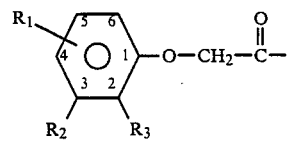

wherein $R_1$, $R_2$, and $R_3$ are each independently selected from the group consisting of hydrogen, halogen, hydrocarbyl having from 1 to 12 carbon atoms, inclusive and halogen substituted hydrocarbyl of 1 to 12 carbon atoms, inclusive: $R_1$ is attached to a carbon atom at one of the ring positions 4, 5 or 6; and $R_2$, and $R_3$ when taken together represent the divalent moiety of the formula:

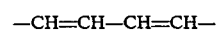

which effectively creates an additional fused aromatic ring structure.

2. The resin of claim 1 wherein the monovalent group is 2,4-dichlorophenoxyacetyl.

3. The resin of claim 1 wherein the monovalent group is 2,4-di-t-butylphenoxyacetyl.

4. The resin of claim 1 wherein the monovalent group is 3,5-di-t-butylphenoxyacetyl.

5. The resin of claim 1 wherein the monovalent group is 2,4-dicumylphenoxyacetyl.

6. The resin of claim 1 wherein $R_2$ and $R_3$ are each hydrogen and $R_1$ is selected from the group consisting of halogen, alkyl of from 1 to 8 carbon atoms, inclusive, and alkaryl of from 7 to 10 carbon atoms, inclusive.

7. The resin of claim 6 wherein $R_1$ represents one of the group consisting of chlorine, methyl, t-butyl, octyl and p-cumyl.

8. A method of regulating the molecular weight of a polycarbonate resin, which comprises; polymerizing a dihydric phenol with a carbonate precursor in the presence of a chain-terminating proportion of a compound selected from those of the formula:

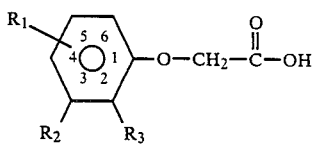

wherein $R_1$, $R_2$ and $R_3$ are each independently selected from the group consisting of hydrogen, halogen, hydrocarbyl from 1 to 12 carbon atoms, inclusive, and halogen—substituted hydrocarbyl of 1 to 12 carbon atoms, inclusive; $R_1$ is attached to a carbon atom at one of the ring positions 4, 5 and 6: $R_2$ and $R_3$, when taken together, are a divalent moiety of the formula:

—CH=CH$_2$—CH=CH—;

which effectively creates an additional fused aromatic ring structure and the acyl halide thereof.

* * * * *

UNITED STATES PATENT AND TRADEMARK OFFICE
CERTIFICATE OF CORRECTION

PATENT NO. : 4,841,015

DATED : June 20, 1989

INVENTOR(S) : Daniel W. Fox, Edward N. Peters, Paul D. Sybert

It is certified that error appears in the above-identified patent and that said Letters Patent is hereby corrected as shown below:

Col. 4
Line 33
"make" should read "making"

Signed and Sealed this

Twenty-fourth Day of July, 1990

Attest:

HARRY F. MANBECK, JR.

Attesting Officer

Commissioner of Patents and Trademarks